United States Patent
Taguchi

(10) Patent No.: US 7,418,075 B2
(45) Date of Patent: Aug. 26, 2008

(54) SUBTLE DYNAMIC HELICAL SCAN FOR UNIFORM Z-RESOLUTION AND NOISE

(75) Inventor: Katsuyuki Taguchi, Cockeysville, MD (US)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 11/331,172

(22) Filed: Jan. 13, 2006

(65) Prior Publication Data

US 2007/0165774 A1 Jul. 19, 2007

(51) Int. Cl.
*A61B 6/00* (2006.01)
(52) U.S. Cl. ............................. 378/15; 378/4
(58) Field of Classification Search ............... 378/4–20, 378/901
See application file for complete search history.

(56) References Cited

U.S. PATENT DOCUMENTS

| 5,390,112 A * | 2/1995 | Tam | 378/17 |
| 7,046,758 B1 * | 5/2006 | Tsuji | 378/15 |
| 2003/0097076 A1 | 5/2003 | Nambu et al. | 600/504 |
| 2004/0086075 A1 | 5/2004 | Hein et al. | 378/4 |

OTHER PUBLICATIONS

Chisato Kondo, et al., Real-Time Volumetric Imaging of Human Heart Without Electrocardiographic Gating by 256—Dectector Row Computed Tomography, Comput. Assist. Tomogr. vol. 29, No. 5, Sep./Oct. 2005, pp. 694-698.

Shinichiro Mori, et al., Clinical Potentials for Dynamic Contrast-Enhanced Hepatic Volumetric Cine Imaging with the Prototype 256—MDCT Scanner, AJR:185, Jul. 2005, pp. 253-256.

Shinichiro Mori, et al., Volumetric Cine Imaging for Cardiovascular Circulation Using Prototype 256—Detector Row Computed Tomography Scanner (4-Dimensional Computed Tomography), A Preliminary Study with a Porcine Model, Comput. Assist. Tomogr., vol. 29, No. 1, Jan./Feb. 2005, pp. 26-30.

Ying Liu, et al., Half-scan cone-beam CT fluoroscopy with multiple x-ray sources, 2001 Am. Assoc. Phys. Med., Medical Physics, vol. 28, No. 7, Jul. 2001, pp. 1466-1471.

Ge Wang, et al., A General Cone-Bream Reconstruction Algorithm, IEEE Transactions on Medical Imaging, vol. 12, No. 3, Sep. 1993, pp. 486-496.

Katsuyuki Taguchi, Temporal resolution and the evaluation of candidate algorithms for four-dimensional CT, Medical Physics, vol. 30, No. 4, Apr. 2003, 2003 Am. Assoc. Phys. Med., pp. 640-650.

(Continued)

*Primary Examiner*—Jurie Yun
(74) *Attorney, Agent, or Firm*—Oblon, Spivak, McClelland, Maier & Neustadt, P.C.

(57) ABSTRACT

A computed tomography apparatus, including: an X-ray helical scanning device including an X-ray generator and an X-ray detector arranged in a gantry, the helical scanning device configured to provide a continuous scan and to obtain projection data of a scanned object arranged on a platform; and control unit configured to control at least one of the X-ray helical scanning device and the platform so as to generate the continuous scan with a helical pitch that is based on a height of a detector row of the X-ray detector projected onto an iso-center of the gantry.

12 Claims, 8 Drawing Sheets

OTHER PUBLICATIONS

Hiroyuki Kudo, et al., Helical-Scan Computed Tomography Using Cone-Beam Projections, Nuclear Science Symposium and Medical Imaging Conference, 1991, Conference Record of the 1991 IEEE, pp. 1958-1962.

L. A. Feldkamp, et al., Practical cone-beam algorithm, 1984 Optical Society of America, J. Opt. Soc. Am. A/vol. 1, No. 6/Jun. 1984, pp. 612-619.

* cited by examiner

SUBTLE DYNAMIC HELICAL SCAN FOR UNIFORM Z-RESOLUTION AND NOISE

BACKGROUND OF THE INVENTION

1. Field of the Invention

The present invention relates generally to a computed tomography (CT) apparatus and the reconstruction of medical images. More particularly, the invention relates to a CT apparatus that uses a plurality of rows of detectors for detecting an image formed by the helical scanning of a subject with a small helical pitch so as to create more uniform noise and resolution in the z-direction.

The present invention includes the use of various technologies referenced and described in the documents identified in the following LIST OF REFERENCES, which are cited throughout the specification by the corresponding reference number in brackets:

LIST OF REFERENCES

[1] Kasuyuki Taguchi, Temporal resolution and the evaluation of candidate algorithms for four dimensional CT, Med. Phys. 30(4), pp. 640-650, April 2003.

[2] Chisato Kondo, et al., Real-time volumetric imaging of human heart without electrocardiographic gating by 256-detector row computed tomography, J Comput Assist Tomogr, Vol. 29, Number 5, pp. 694-698, September/October 2005.

[3] Shinichiro Mori, et al., Clinical Potentials for Dynamic Contrast-Enhanced Hepatic Volumetric Cine Imaging with Prototype 256-MDCT Scanner, AJR: 185, pp. 253-256, July 2005.

[4] Shinichiro Mori, et al., Volumetric Cine Imaging for Cardiovascular Circulation Using Prototype 256-Dectector Row Computed Tomography Scanner (4-Dimensional Computed Tomgraphy), J Comput Assist Tomogr, Vol. 29, Number 1, pp. 26-30, January/February 2005.

[5] Ying Lu, et al., Half-scan cone-beam CT fluoroscopy with multiple x-ray sources, Med. Phys. 28 (7), pp. 1466-1471, July 2001.

[6] Ge Wang, et al., A General Cone-Beam Reconstruction Algorithm, IEEE Transactions on Medical Imaging, Vol. 12, No. 3, pp. 486-496, September 1993.

[7] H. Kudo and T. Saito, Helical-scan computed tomography using cone-beam projections, Nuclear Science Symposium and Medical Imaging Conference, pp. 1958-1962, November 1991.

[8] L. A. Feldkamp, et al., Practical cone-beam algorithm, J. Opt Soc. Am A/Vol. 1, No. 6, pp. 612-619, June 1984.

[9] Hein et al., U.S. Patent Publication No. 2004/0086075.

[10] Nambu et al., U.S. Patent Publication No. 2003/0097076.

The entire contents of each reference listed in the above LIST OF REFERENCES are incorporated herein by reference.

DISCUSSION OF THE BACKGROUND

Dynamic cone-beam (4D) scanning has recently drawn increased interest. Dynamic cone beam (4D) scanning requires that the same location of an organ of interest be constantly scanned for a certain period of time. Thus, a circular scan is desired.

In a conventional CT apparatus, a circular scan with discrete detectors generates a z-axis dependent resolution due to discrete sampling and interpolation. At the center of an interpolation cell, no interpolation in the z-direction is necessary. However, at voxels between two cells, the interpolation in the z-direction is always required. This may be referred to as the "sweet-and-sore-spot phenomena." FIG. 1 graphically depicts the "sweet-and-sore-spot phenomena" by the plurality of alternating "hot spot" and "cold spot" regions along the z-axis. FIG. 1 depicts the arrangement of hot spots and cold spots for $\beta=0$, and the arrangement of hot spots and cold spots for $\beta=\pi$, where $\beta$ is the scan angle.

At the iso-center, the sampling patterns (i.e., the position of cold spots and hot spots) $\pi$ radians apart match each other, as shown in FIG. 1. Thus, circular scans result in the reconstructed image having a strong noise variation along the z-axis.

Conventional methods have attempted to overcome the above-noted problem by attempting to use a helical scan with a pitch of 0.5-1.5 (1/rev). However, this is not acceptable because the organ of interest is scanned only for a limited period of time. More precisely, the organ of interest is scanned for $1/1.5$-$1/0.5$ $t_{rot}$, where $t_{rot}$ is the time period per gantry rotation (s/rev).

As noted above, the conventional method results in strong noise variation along the z-axis. The z-resolution and the image noise are a function of z-axis position in a circular scan. FIG. 2 shows a plot comparing the standard deviation (image noise) normalized by the standard deviation of fan-beam reconstruction ($\sigma_0$) along the z-axis (i.e., $\sigma_{cone-beanm}/\sigma_0$) with the z-resolution. As shown in FIG. 2, the image noise is as large as fan-beam reconstruction at the center of the detector rows (i.e., near the middle of two tick marks). FIG. 2 also shows that the image noise is approximately 70% (or $1/\sqrt{2}$) of fan-beam reconstruction in between two detectors rows (i.e., on each tick mark). The z-resolution shows the opposite phenomena; the resolution at the center of the detector rows is as good as fan-beam reconstruction, while the resolution is about twice as broad when in between two detector rows.

Conventional dynamic helical scanning methods are known to repeat 2 to 5 helical scans over the same volume. Conventional dynamic techniques use repeated scans to provide variation in the volume of interest over time. However, temporal resolution (time increment) is limited. For example, the liver is scanned 30, 60, 90, and 300 seconds after the contrast material is injected in order to observe the hepatic artery phase, the portal vein phase, hepatic vein phase, and balanced phase, respectively. The time resolution is about 30 seconds in this case. Thus, this repeated scan technique is not an acceptable method of correcting the sweet-and-sore-spot phenomena noted above.

As shown in FIGS. 3 and 4 of reference [1], the results of the conventional technique of using z-increment (pitch) of 0.5 (mm/slice) are shown. FIGS. 3 and 4 of reference [1] clearly show that the images are blurred due to insufficient temporal resolution.

Reference [2] acknowledges that noise and irregularities appeared in their result images because of limited time resolution.

References [3] and [4] describe a prototype 256-MDCT with a wide-area cylindrical 2D detector. The development of the 16-MDCT made dynamic 3D imaging possible. However, the craniocaudal coverage of the 16-MDCT scanner's detector, without gantry movement, imposes a limit on cine imaging. The prototype 256-MDCT was developed to make cine imaging with a wider coverage. However, the 256-MDCT scans continuously at the same position (i.e., table remains stationary). Thus, the 256-MDCT suffers from the sweet-and-sore-spot phenomena noted above.

Furthermore, studies have been conducted on how to fill out the 3D Radon space using a continuous function. However, no study has been conducted to investigate the discrete nature of each sample obtained in a CT scan, which is the cause of the sweet-and-sore-spot phenomena noted above.

SUMMARY OF THE INVENTION

Accordingly, to overcome the above-noted problems, the present invention seeks to provide a method, apparatus, and computer program product for producing images that are space-independent, have uniform z-resolution, and have uniform noise in the z-direction.

According to a first aspect of the present invention, there is provided a computed tomography apparatus, including: an X-ray helical scanning device including an X-ray generator and X-ray detector arranged in gantry, the helical scanning device configured to provide a continuous scan and to obtain projection data of a scanned object arranged on a platform; and a control unit configured to control at least one of the X-ray helical scanning device and the platform so as to generate the continuous scan with a helical pitch that is based on a height of a detector row of the X-ray detector projected onto an iso-center of the gantry.

According to a second aspect of the present invention, the control unit of the computed tomography apparatus is configured to generate the scan in which the helical pitch is equal to the height of the detector row of the X-ray detector projected onto an iso-center of the gantry.

According to a third aspect of the present invention, the control unit of the computed tomography apparatus is configured to generate the scan in which the helical pitch is equal to one-half of the height of the detector row of the X-ray detector projected onto an iso-center of the gantry.

According to a fourth aspect of the present invention, the computed tomography apparatus further includes an image reconstructing device configured to reconstruct an image based on the obtained projection data using cone-beam reconstruction.

According to a fifth aspect of the present invention, the control unit of the computed tomography apparatus is configured to generate the scan in which a period of time spent imaging a given volume of the object is defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is the time period per gantry rotation, D is the detector height at the iso-center, and H is the helical pitch.

According to a sixth aspect of the present invention, a method of performing computed tomography, includes: obtaining projection data of a scanned object arranged on a platform using an X-ray helical scanning device including an X-ray generator and X-ray detector arranged in a gantry configured to perform a continuous scan of the object, wherein the obtaining step includes controlling movement of at least one of the X-ray device and the platform so as to generate the continuous scan with a helical pitch that is based on a height of a detector row of the X-ray detector projected onto an iso-center of the gantry.

According to a seventh aspect of the present invention, the helical pitch in the method of performing computed tomography is equal to the height of the detector row of the X-ray detector projected onto an iso-center of the gantry.

According to an eighth aspect of the present invention, the helical pitch in the method of performing computed tomography is equal to one-half of the height of the detector row of the X-ray detector projected onto an iso-center of the gantry.

According to a ninth aspect of the present invention, the method of performing computed further includes reconstructing an image based on the projection data using cone-beam reconstruction.

According to a tenth aspect of the present invention, the method of performing computed further includes imaging a given volume of the object for a period of time defined $$\text{by } t_{cov}(z_{vol}) = \frac{(D - z_{vol}) \cdot t_{rot}}{H},$$

in which $t_{cov}$ is time coverage, $z_{vol}$ is the given volume, $t_{rot}$ is the time period per gantry rotation, D is the detector height at the iso-center, and H is the helical pitch.

According to an eleventh aspect of the present invention, a computer readable medium stores instructions for execution on a computer system, which when executed by the computer system, causes the computer system to perform steps including: obtaining projection data of a scanned object arranged on a platform using an X-ray helical scanning device including an X-ray generator and X-ray detector arranged in a gantry configured to perform a continuous scan of the object, wherein the obtaining step includes controlling movement of at least one of the X-ray device and the platform so as to generate the continuous scan with a helical pitch that is based on a height of a detector row of the X-ray detector projected onto an iso-center of the gantry.

Additional objects and advantages of the invention will be set forth in the description which follows.

BRIEF DESCRIPTION OF THE DRAWINGS

A more complete appreciation of the embodiments of the invention, and many of the attendant advantages thereof, will be readily obtained as the same becomes better understood by reference to the following detailed description, when considered in connection with the accompanying drawings, wherein.

DETAILED DESCRIPTION OF THE PREFERRED EMBODIMENTS

Figure 3:
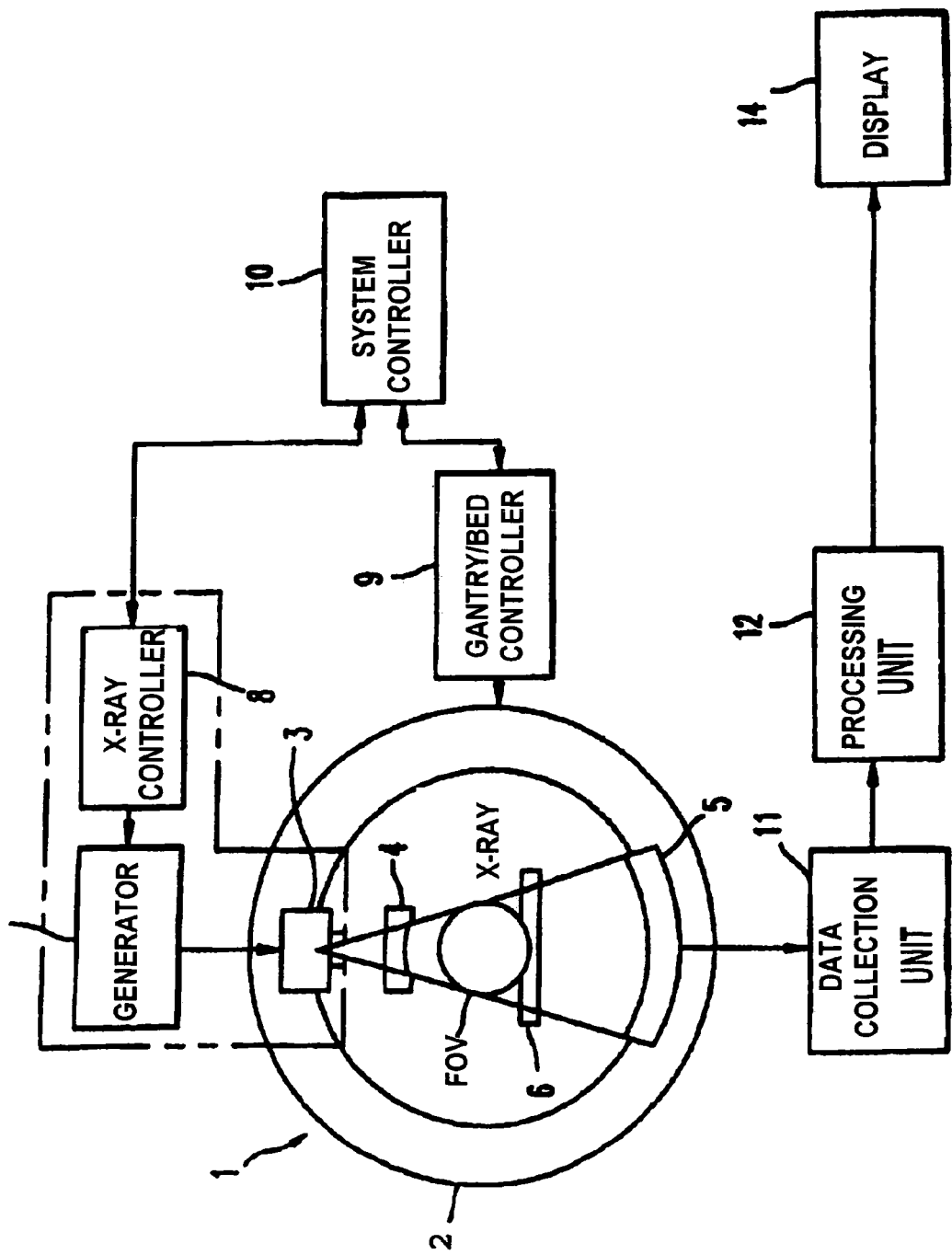
FIG. 3 illustrates a CT-apparatus.

Referring now to the drawings, wherein like reference numerals designate identical or corresponding parts throughout the several views, FIG. 3 shows an x-ray computed-tomographic imaging device that can be used to obtain data that is processed by methods of the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in a two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed or platform 6. Two-dimensional array type x-ray detector 5 is mounted on rotating ring 2. Each detector element corresponds to one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 based on the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which the X-ray source moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal to produce projection data. The projection data that is output from data collection unit 11 is fed to reconstruction processing unit 12. Reconstruction processing unit 12 uses the projection data to find backprojection data reflecting the x-ray absorption in each voxel. In the helical scanning system using a cone-beam of x-rays, the imaging region (effective field of view) is a cylindrical shape with radius $\omega$ centered on the axis of revolution. Reconstruction processing unit 12 defines a plurality of voxels in this imaging region, and finds the backprojection data for each voxel. The three-dimensional image data or tomographic image data compiled by using this backprojection data is sent to display device 14, where it is displayed visually as a three-dimensional image or tomographic image.

For the purposes of this description we shall define an image to be a representation of a physical scene, in which the image has been generated by some imaging technology. Examples of imaging technology could include television or CCD cameras or X-ray, sonar or ultrasound imaging devices. The initial medium on which an image is recorded could be an electronic solid-state device, a photographic film, or some other device such as a photostimulable phosphor. That recorded image could then be converted into digital form by a combination of electronic (as in the case of a CCD signal) or mechanical/optical means (as in the case of digitizing a photographic film or digitizing the data from a photostimulable phosphor).

Figure 4:
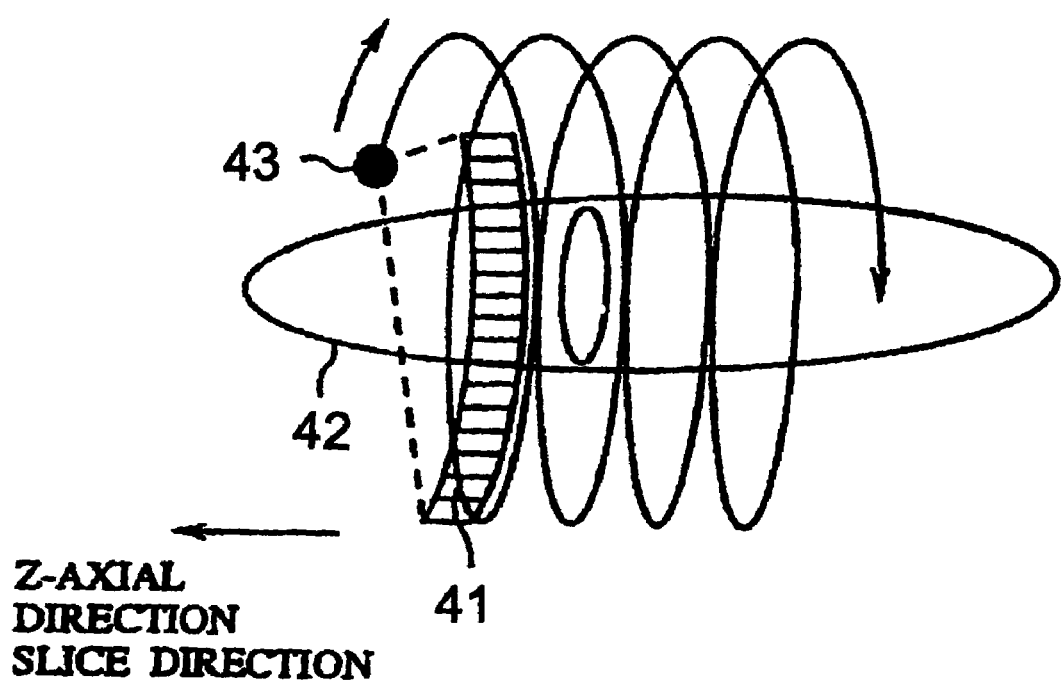
FIG. 4 is a CT scanning system showing a helical pitch.

To overcome the sweet-and-sore-spot phenomena of the conventional techniques, a subtle helical scan is implemented. The subtle helical scan conducts a helical scan with an extremely small helical pitch. As shown in FIG. 4, a CT-apparatus based on a subtle helical scan collects tomographic image data of a subject to be examined by moving a subject on a platform in a body axial direction of subject 42, along the z-axis, in synchronization with a continuous rotation of radiation source 43 and a detector 41.

In a first embodiment of the present invention, an extremely small helical pitch is used. The helical pitch corresponds to the height of one detector row at the iso-center.

The sweet-and-sore-spot phenomena noted above results from the sampling pattern of the data acquisition. In a circular scan (or a helical scan with a pitch of zero), voxels at the z-axis have a constant sampling pattern. For some voxels, cone-beam data from two detector rows are axially interpolated with a weight of 0.5 each over the entire projection angular range. The interpolation results in some of the voxels being blurred along the z-axis; while other voxels have a weight of 1.0 and 0.0 for sharp resolution.

Figure 5:
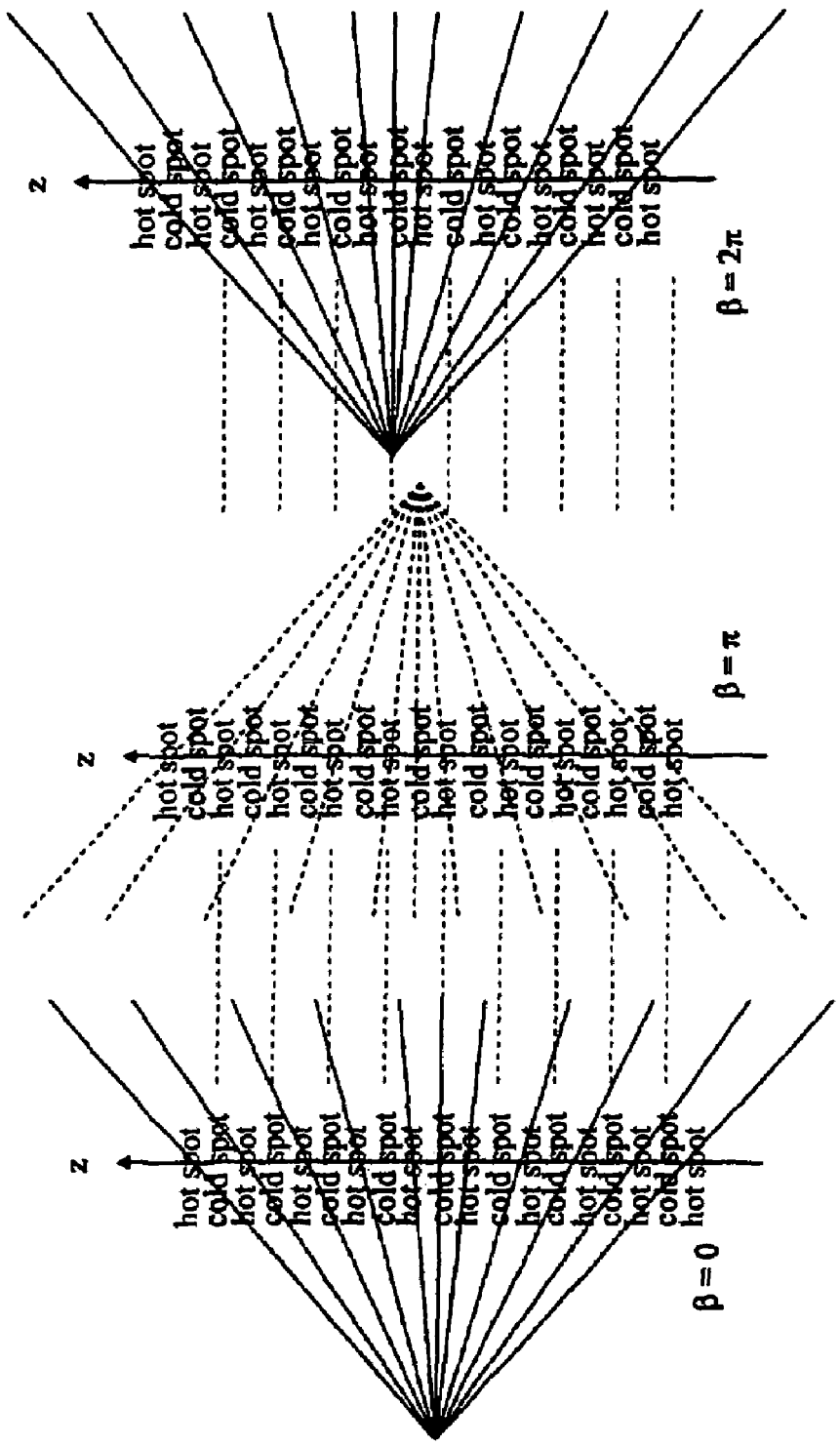
FIG. 5 illustrates three sampling patterns used with a first embodiment of the present invention.

As shown in FIG. 5, by using a helical pitch equal to one detector row at the iso-center, the sampling pattern of the cone-beam data obtained at 180 degrees ($\beta=\pi$) is different from the original sampling pattern ($\beta=0$). FIG. 5 shows that a cold spot in the sampling pattern at $\beta=0$ matches to a hot spot in the sampling pattern at $\beta=\pi$. By choosing a very small helical scan pitch w (i.e., table increment=w (mm/rev)), instead of no motion at all in the z-axis, cold/hot spots are shifted in the z-direction, as shown in FIG. 5.

Figure 1:
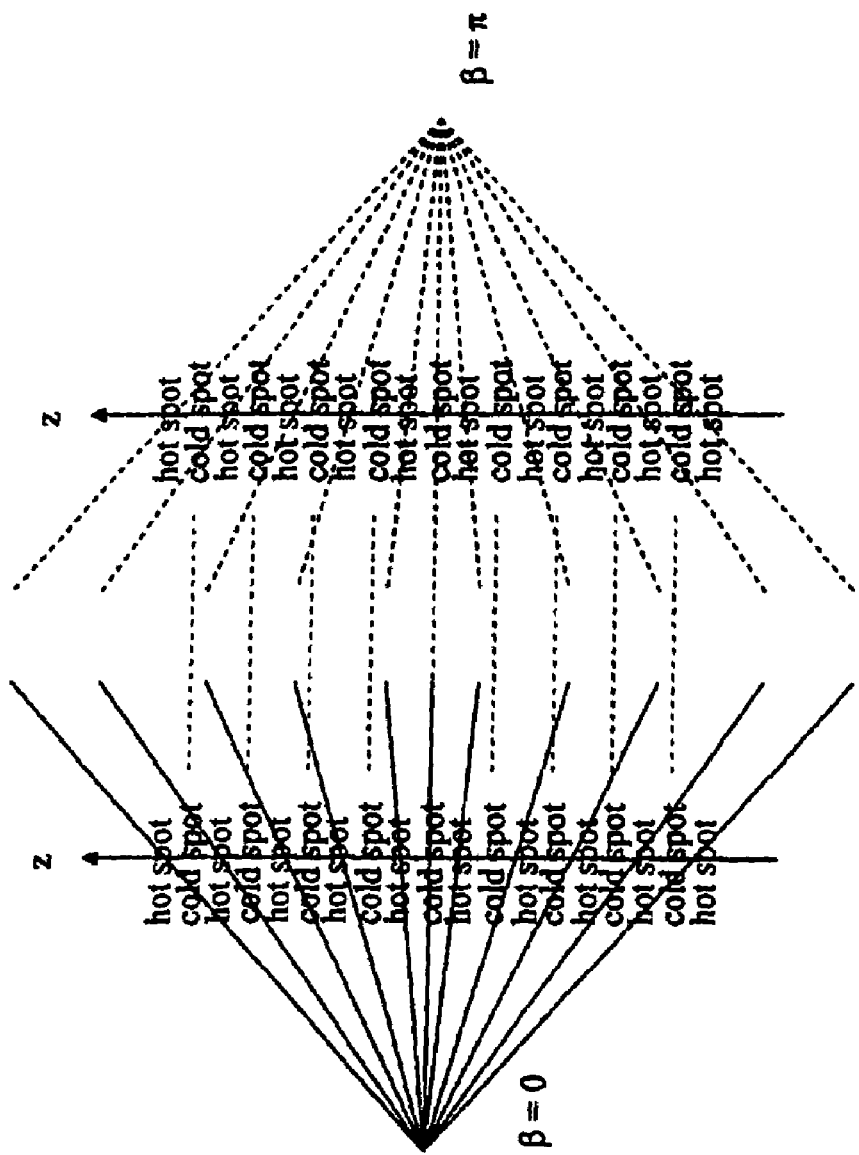
FIG. 1 illustrates two sampling patterns used with a conventional CT-apparatus.
Figure 2:
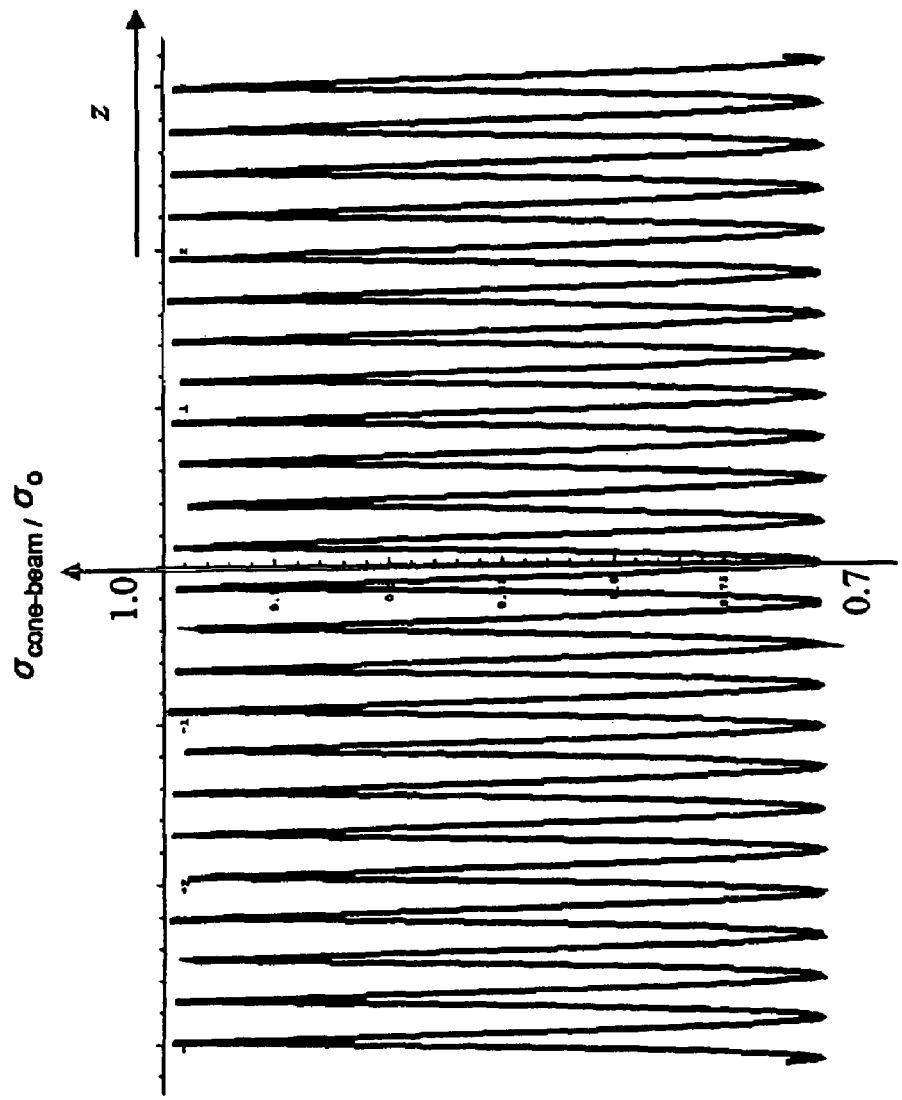
FIG. 2 illustrates a plot of z-resolution vs. image noise.

Because 180-degree-apart data are known to be complementary, even with the existence of the cone-angle, a plot of z-resolution versus image noise, similar to FIG. 2, would show reduced amplitude of the zigzag pattern.

Accordingly, it can appreciated that $$g(\beta,\gamma,\alpha) \approx g(\beta+\pi+2\gamma,-\gamma,\alpha') \tag{1}$$

where $\beta$ is the projection-angle, $\gamma$ is the ray angle, and $\alpha$ is the cone angle, respectively. Although the similarity decreases with increasing $\alpha$, the subtle helical scan remains a good approximation.

Furthermore, if the cone angle is large enough, that is, if the number of detector rows is large enough, the subtle helical scan provides a reasonably long period of time to image the volume of interest. For example, the time-coverage $t_{cov}$ of a given volume $z_{vol}$ is provided by $$t_{cov}(z_{vol}) = \frac{(D-z_{vol}) \cdot t_{rot}}{H}, \tag{2}$$

where D is the detector height at the iso-center [mm], and H is the helical pitch [mm/rev]. Thus, if the number of the detector row is 256, $z_{vol}$ is 50 mm, and H (=w) is 0.5 mm, then $t_{cov}$ is 78 seconds.

Figure 6:
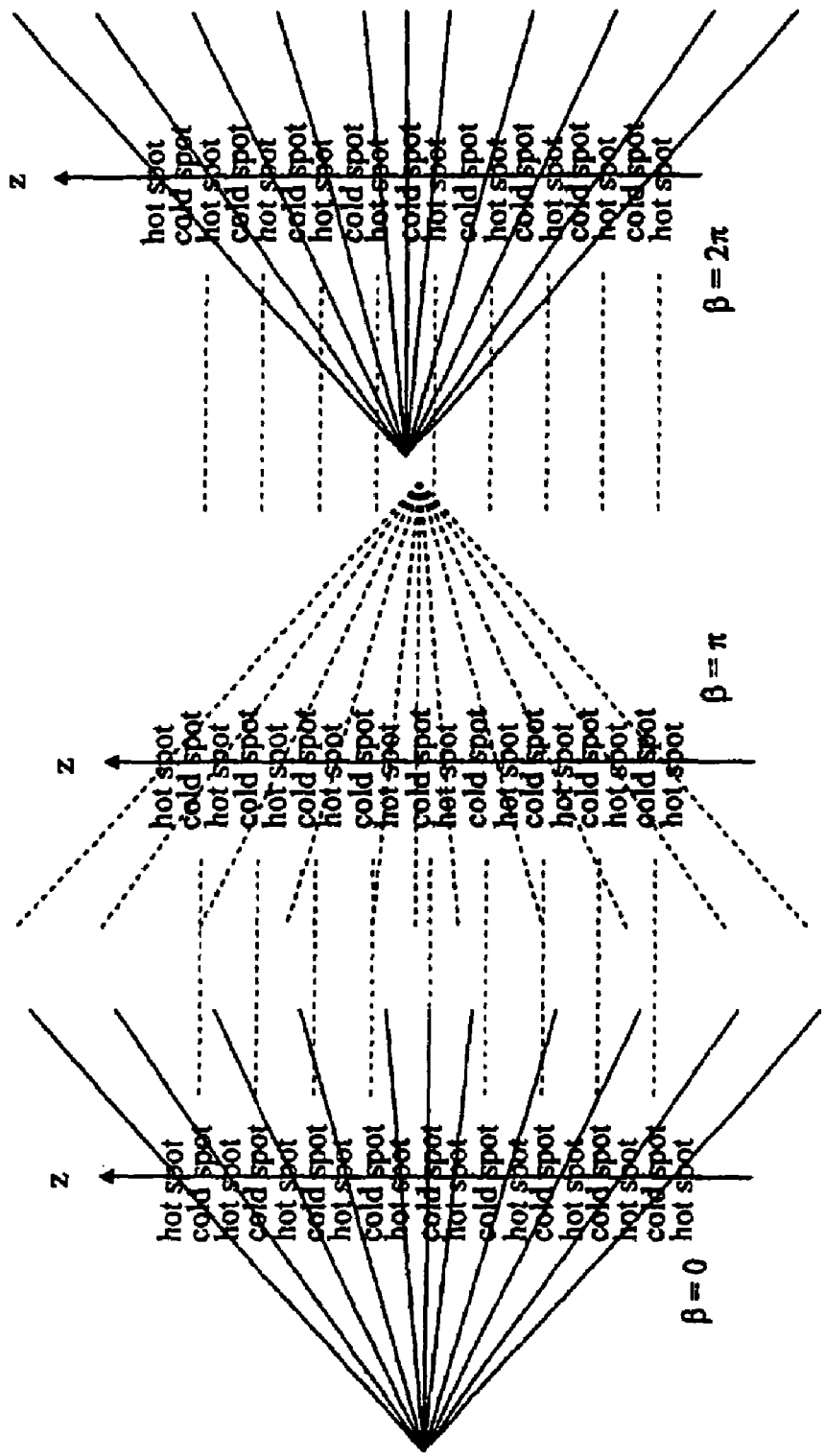
FIG. 6 illustrates three sampling patterns used with a second embodiment of the present invention.

In a second embodiment of the present invention, the helical pitch is made to correspond to the height of one-half a detector row at the iso-center. FIG. 6 shows sampling patterns used in the second embodiment of the present invention.

As shown in FIG. 6, the sampling patterns at $\beta=0$ and $\beta=\pi$, are different from each other. However, because the helical pitch is set at one-half a detector row, the interlacing of hot and cold spots shown in FIG. 6 is not as close as in the first embodiment shown in FIG. 5. However, we note that the hot spot in the sampling pattern $\beta=0$ matches the cold spot in the sampling pattern for $\beta=2\pi$ (not $\pi$). Because of the similarity of the cone-beam projection data at $\beta=0$ and $\beta=2\pi$, the second embodiment provides better results than the conventional techniques. Our concern is the fact that, the technique of the second embodiment may only help $\beta=0$, and may not be good for other angles.

Image reconstruction may be done using known cone-beam reconstruction techniques, which are described in reference [8] with weightings.

For fan-beam reconstruction, the incremental contribution to the reconstructed density from the projection data for a small increment in rotation angle is determined. From the projection data along an intersection of the detector plane and the midplane (Z=0), the contribution points that lie in the midplane can be calculated. The projections that intersect the detector plane along a line parallel to the midplane, but not in it (constant, non-zero Z), themselves define a plane. This plane is treated as if it were the midplane of another, tilted arrangement. If a complete set of projections (i.e., all rotation angles about the normal) for such a tilted plane, we could reconstruct the density for this plane by using the Radon transform. This would entail sweeping the source around the sample along a circle in the tilted plane.

For cone-beam reconstruction, the difference between the actual rotation about the vertical axis and the equivalent rotation about the normal to the plane must be corrected for. Further, the source-to-detector distance in the tilted plane must be substituted into the Radon transform. After making these corrections, the increment of reconstructed density is obtained.

The total density at a point r is taken to be the sum of the incremental contributions from all planes (one for each rotation angle) that pass through r. The planes of projection that contribute to the reconstruction at a given r may be visualized as forming a sheaf. Except for points in the midplane, the sheaf for each reconstruction point is unique.

As can appreciated by those of ordinary skill in the art, other fan beam reconstruction algorithms may also be used in conjunction with the present invention.

Figure 7:
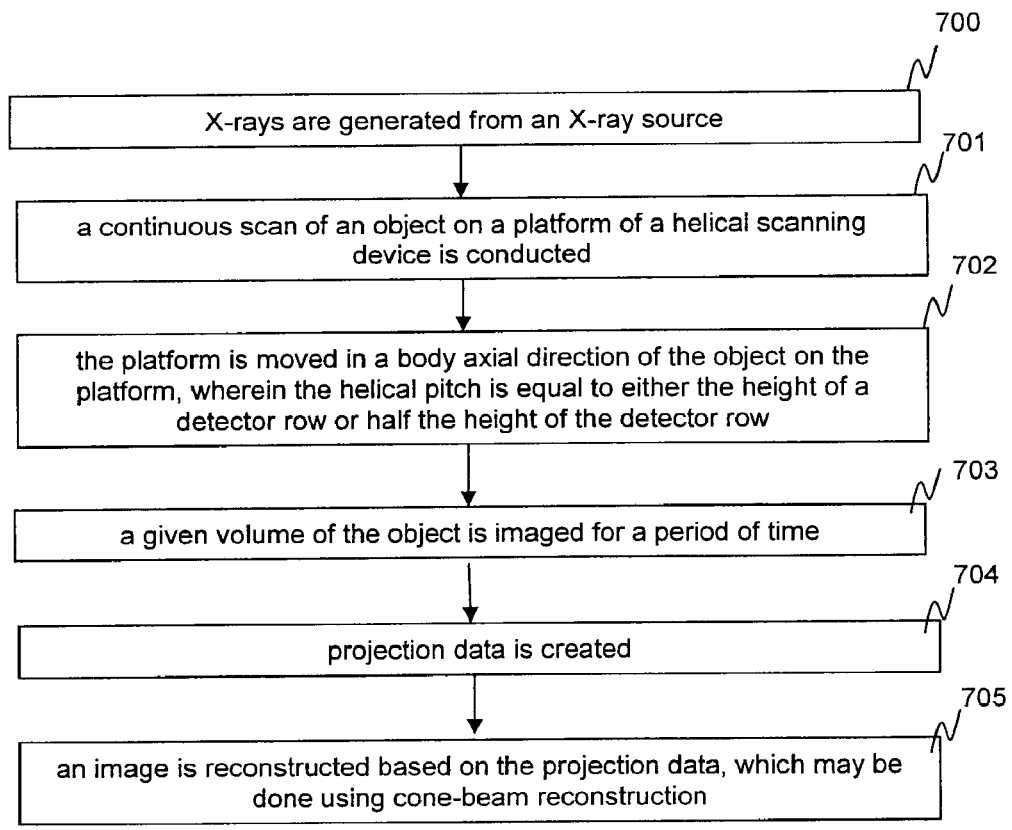
FIG. 7 illustrates a method used to perform computed tomography.

FIG. 7 illustrates a method of computed tomography for an embodiment of the claimed invention. In step 700, X-rays are generated from an X-ray source. In step 701, a continuous scan of an object on a platform of a helical scanning device is conducted. In step 702, the platform is moved in a body axial direction of the object on the platform. The helical pitch created by the movement of the platform may be equal to either of the height of a detector row or one-half the height of a detector row. In step 703, a given volume of the object is imaged for a period of time. In step 704, projection data is collected. In step 705, an image is reconstructed based on the projection data, which may be done using cone-beam reconstruction.

Figure 8:
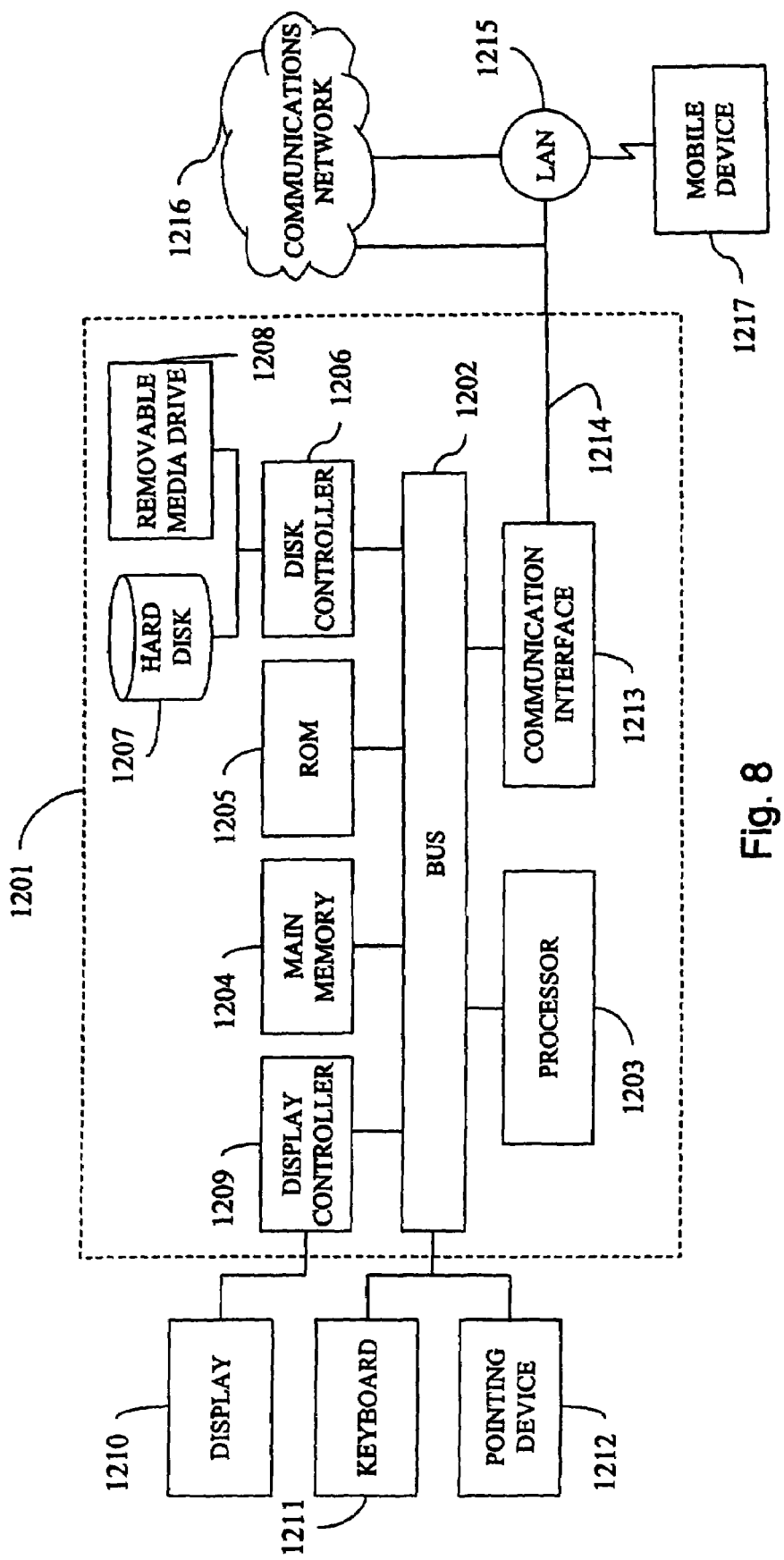
FIG. 8 is a block diagram of a computer system upon which an embodiment of the present invention may be implemented.

FIG. 8 illustrates a computer system 1201 upon which an embodiment of the present invention may be implemented. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

All embodiments of the present invention may conveniently be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory, and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Stored on any one or on a combination of the above-noted or any other computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Furthermore, the source of image data to the present invention may be any appropriate image acquisition device such as an X-ray machine or CT apparatus. The acquired data may be digitized if not already in digital form.

Numerous modifications and variations of the present invention are possible in light of the above teachings. It is therefore to be understood that within the scope of the appended claims, the invention may be practiced otherwise than as specifically described herein.

What is claimed is:

1. A computed tomography apparatus, comprising:
    an X-ray helical scanning device including an X-ray generator and a two-dimensional X-ray detector arranged in a gantry, the X-ray helical scanning device configured to provide a continuous scan and to obtain projection data of a scanned object arranged on a platform; and
    a control unit configured to control at least one of the X-ray helical scanning device and the platform so as to generate the continuous scan with a helical pitch that is equal to a height of one detector row of the X-ray detector,
    wherein the control unit is configured to generate the continuous scan so that a period of time spent imaging a given volume of the object is defined by $$t_{cov}(z_{vol}) = \frac{(D - z_{vol}) \cdot t_{rot}}{H},$$

in which $t_{cov}$ is time coverage, $z_{vol}$ is the given volume. $t_{rot}$ is time period per gantry rotation, D is the detector height, and H is the helical pitch.

2. The computed tomography apparatus of claim 1, further comprising:
    an image reconstructing device configured to reconstruct an image based on the obtained projection data using cone-beam reconstruction.

3. A computed tomography apparatus, comprising:
    an X-ray helical scanning device including an X-ray generator and a two-dimensional X-ray detector arranged in a gantry, the X-ray helical scanning device configured to provide a continuous scan and to obtain projection data of a scanned object arranged on a platform; and
    a control unit configured to control at least one of the X-ray helical scanning device and the platform so as to generate the continuous scan with a helical pitch that is equal to one-half of a height of one detector row of the X-ray detector,
    wherein the control unit is configured to generate the continuous scan so that a period of time spent imaging a given volume of the object is defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

4. A computed tomography apparatus, comprising:
    an X-ray helical scanning device including an X-ray generator and a two-dimensional X-ray detector arranged in a gantry, the X-ray helical scanning device configured to provide a continuous scan and to obtain projection data of a scanned object arranged on a platform; and
    means for controlling movement of at least one of the X-ray helical scanning device and the platform so as to generate the continuous scan with a helical pitch that is equal to a height of one detector row of the X-ray detector,
    wherein the means for controlling generates the continuous scan so that a period of time spent imaging a given volume of the object is defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

5. The computed tomography apparatus of claim 4, further comprising:
    an image reconstructing device configured to reconstruct an image based on the obtained projection data using cone-beam reconstruction.

6. A computed tomography apparatus, comprising:
    an X-ray helical scanning device including an X-ray generator and a two-dimensional X-ray detector arranged in a gantry, the X-ray helical scanning device configured to provide a continuous scan and to obtain projection data of a scanned object arranged on a platform; and
    means for controlling movement of at least one of the X-ray helical scanning device and the platform so as to generate the continuous scan with a helical pitch that is equal to one-half of a height of one detector row of the X-ray detector,
    wherein the means for controlling generates the continuous scan so that a period of time spent imaging a given volume of the object is defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

7. A method of performing computed tomography, comprising:
    obtaining projection data of a scanned object arranged on a platform using an X-ray helical scanning device including an X-ray generator and a two-dimensional X-ray detector arranged in a gantry configured to perform a continuous scan of the object,
    wherein the obtaining step includes controlling movement of at least one of the X-ray helical scanning device and the platform so as to generate the continuous scan with a helical pitch that is equal to a height of one detector row of the X-ray detector; and
    imaging a given volume of the object for a period of time defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

8. The method of claim 7, further comprising:
    reconstructing an image based on the obtained projection data using cone-beam reconstruction.

9. A method of performing computed tomography, comprising:
- obtaining projection data of a scanned object arranged on a platform using an X-ray helical scanning device including an X-ray generator and a two-dimensional X-ray detector arranged in a gantry configured to perform a continuous scan of the object,
- wherein the obtaining step includes controlling movement of at least one of the X-ray helical scanning device and the platform so as to generate the continuous scan with a helical pitch that is equal to one-half of a height of one detector row of the X-ray detector; and
- imaging a given volume of the object for a period of time defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

10. A computer readable medium storing instructions for execution on a computer system, which when executed by the computer system, causes the computer system to perform steps comprising:
- obtaining projection data of a scanned object arranged on a platform using an X-ray helical scanning device including an X-ray generator and a two-dimensional X-ray detector arranged in a gantry configured to perform a continuous scan of the object,
- wherein the obtaining step includes controlling movement of at least one of the X-ray helical scanning device and the platform so as to generate the continuous scan with a helical pitch that is equal to a height of one detector row of the X-ray detector; and
- imaging a given volume of the object for a period of time defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

11. The computer readable medium of claim 10, further comprising:
- reconstructing an image based on the projection data using cone-beam reconstruction.

12. A computer readable medium storing instructions for execution on a computer system, which when executed by the computer system, causes the computer system to perform steps comprising:
- obtaining projection data of a scanned object arranged on a platform using an X-ray helical scanning device including an X-ray generator and a two-dimensional X-ray detector arranged in a gantry configured to perform a continuous scan of the object,
- wherein the obtaining step includes controlling movement of at least one of the X-ray helical scanning device and the platform so as to generate the continuous scan with a helical pitch that is equal to one-half of a height of one detector row of the X-ray detector; and
- imaging a given volume of the object for a period of time defined by $$t_{cov}(z_{vol}) = \frac{(D - z_{vol}) \cdot t_{rot}}{H},$$

in which $t_{cov}$ is time coverage, $z_{vol}$ is the given volume, $t_{rot}$ is time period per gantry rotation, D is the detector height, and H is the helical pitch.

* * * * *